United States Patent [19]

Gonczy et al.

[11] Patent Number: 5,105,626
[45] Date of Patent: Apr. 21, 1992

[54] APPARATUS FOR MEASURING TENSILE AND COMPRESSIVE PROPERTIES OF SOLID MATERIALS AT CRYOGENIC TEMPERATURES

[75] Inventors: John D. Gonczy, Oaklawn; Finley W. Markley, St. Charles; William R. McCaw, Burr Ridge; Ralph C. Niemann, Downers Grove, all of Ill.

[73] Assignee: Universities Research Association, Inc., Washington, D.C.

[21] Appl. No.: 643,423

[22] Filed: Jan. 22, 1991

[51] Int. Cl.⁵ .................................................. F25B 19/00
[52] U.S. Cl. .............................................. 62/511; 73/818; 73/826
[58] Field of Search .................... 73/818, 826; 62/51.1

[56] References Cited

U.S. PATENT DOCUMENTS

| | | | |
|---|---|---|---|
| 4,346,754 | 8/1982 | Imig et al. | 62/51.1 |
| 4,696,169 | 9/1987 | Niemann et al. | 62/51.1 |
| 4,781,034 | 11/1988 | Nicol et al. | 62/51.1 |

Primary Examiner—Ronald C. Capossela
Attorney, Agent, or Firm—McAndrews, Held & Malloy, Ltd.

[57] ABSTRACT

An apparatus for evaluating the tensile and compressive properties of material samples at very low or cryogenic temperatures employs a stationary frame and a dewar mounted below the frame. A pair of coaxial cylindrical tubes extend downward towards the bottom of the dewar. A compressive or tensile load is generated hydraulically and is transmitted by the inner tube to the material sample. The material sample is located near the bottom of the dewar in a liquid refrigerant bath. The apparatus employs a displacement measuring device, such as a linear variable differential transformer, to measure the deformation of the material sample relative to the amount of compressive or tensile force applied to the sample.

12 Claims, 3 Drawing Sheets

APPARATUS FOR MEASURING TENSILE AND COMPRESSIVE PROPERTIES OF SOLID MATERIALS AT CRYOGENIC TEMPERATURES

This invention was made with Government support under Contract No. DE-AC02-76CH03000, awarded by the United States Department of Energy. The Government has certain rights in the invention.

FIELD OF THE INVENTION

This invention relates to an apparatus for measuring tensile and compressive properties of solid materials at cryogenic temperatures. More particularly, this invention relates to an apparatus for measuring the dimensional response of a deformable material to the application of compressive and tensile forces at cryogenic temperatures. Forces are transmitted through concentric cylindrical tubes to the material sample to be studied, which is supported near the bottom of a dewar.

BACKGROUND OF THE INVENTION

The design of devices that operate at very low temperatures including, for example, the proposed Superconducting Super Collider (SSC), has brought about the need for the development and selection of materials that will operate effectively at low temperatures. The performance of known materials and newly developed materials proposed for use in cryogenic environments like the SSC must be tested at correspondingly low temperatures. The present apparatus permits the evaluation of the tensile and compressive properties of such cryogenic materials.

Cryogenic support systems have been developed using a technique known as shrink-fitting. See U.S. Pat. Nos. 4,696,169 and 4,781,034, incorporated herein by reference. It is known, for example, that cryogenic support members can be constructed of a non-metallic rod or tube and a metallic end connection assembled to the tube. The metallic end connection comprises a metallic plug which conforms to the shape of the interior surface of the tube and a metallic sleeve that is positioned over the exterior surface of the tube. The plug and the sleeve are shrink-fitted to the rod or tube to produce a connection that is effective under conditions of compression, tension and bending.

The process of shrink-fitting takes advantage of the differences in the coefficients of thermal expansion of the materials forming the tube, plug and sleeve. In the above example for cryogenic support members, the metallic plug can be cooled so that it shrinks in size. The metallic sleeve can be heated so that it expands in size. The cooled metallic plug is inserted into the interior of one end of the tube maintained at ambient temperature, and the warmed metallic sleeve is slipped over the exterior of the tube at the same end. As the three components (plug, tube, and sleeve) reach thermal equilibrium, the plug expands and exerts an outward force against the interior wall of the tube while the sleeve contracts and exerts an inward force against the exterior wall of the tube. The plug and the sleeve thus exert oppositely directed and substantially counterbalanced forces against each other and against the tube. The tube remains structurally stable, and the plug and sleeve remain firmly in place at the end of the tube, forming a secure end connection.

If the coefficient of thermal expansion of the plug is less than the coefficient of thermal expansion of the tube, and the coefficient of thermal expansion of the tube is less than the coefficient of thermal expansion of the sleeve, then the tube, plug and sleeve may be warmed together to the same, or approximately the same, temperature, and the plug and sleeve then shrink-fitted to the tube. As the plug, tube and sleeve are warmed together, the plug expands less because of its lower coefficient of thermal expansion. The warmed plug is fitted into the interior of the tube while the warmed sleeve, in its expanded state because of its high coefficient of thermal expansion, is slipped over the tube. As all three components are cooled, the tube shrinks at a greater rate than the plug, and the sleeve shrinks at a greater rate than the tube. The plug exerts an outwardly directed force against the inner wall of the tube while the sleeve exerts an inwardly directed force against the outer wall of the tube. The forces exerted by the plug and the sleeve substantially counterbalance each other, and a secure end connection is formed.

The present apparatus utilizes shrink-fitting to attach the annular sleeves and plugs to the coaxial inner and outer tubes. Specifically, with respect to the outer tube, an annular sleeve is shrink-fitted over the upper end of the outer tube to provide a means for suspending the outer tube from the stationary frame. An annular plug is shrink-fitted inside the outer tube at the upper end to counterbalance the force exerted by the sleeve. With respect to the inner tube, an annular sleeve is shrink-fitted over the upper end of the inner tube to provide a site for attaching the inner tube to the dome member which transmits the compressive and tensile forces to the material sample. An annular plug is shrink-fitted inside the upper end of the inner tube to counterbalance the force exerted against the tube by the sleeve.

OBJECTS OF THE INVENTION

An object of the invention is to provide an apparatus for measuring the compressive and tensile properties of deformable material samples at cryogenic temperatures.

Another object of the invention is to provide an apparatus for measuring the tensile and compressive properties of solid materials at cryogenic temperatures in which there is low heat leak to the cryogenic environment.

Further and additional objects will appear from the description, accompanying drawings and appended claims.

SUMMARY OF THE INVENTION

These and other objects are achieved by an apparatus for measuring the deformation of a material sample in response to the application of compressive and tensile force at cryogenic temperatures. The apparatus comprises a stationary frame maintained at ambient temperature. A dewar is mounted below the frame, and maintains a cryogenic environment within the dewar. An outer cylindrical tube extends downwardly within the dewar. The upper end of the outer tube is fixedly attached to the frame.

The apparatus further comprises a bottom plate fixedly attached to the lower end of the outer tube. The bottom plate is adapted to support the material sample. An inner cylindrical tube extends downwardly within the outer tube. The lower end of the inner tube is adapted to transmit force to the material sample. A predetermined force is applied to the upper end of the inner cylindrical tube, and the deformation of the material sample is measured relative to the bottom plate.

In the preferred embodiment, each of the ends of the inner and outer tubes has an annular plug fitted within its interior surface and an annular sleeve fitted over its exterior surface. The annular sleeve at the upper end of the outer tube is preferably attached to the frame. The annular plugs and annular sleeves are preferably attached to the inner and outer tubes by shrink-fitting.

The apparatus preferably further comprises insulation inserted in the voids formed between the dewar and the outer tube, between the outer tube and the inner tube, and within the inner tube.

In the preferred embodiment, the means for measuring the deformation of the material sample is a linear variable differential transformer having a first probe and a second probe. The probes extend downwardly within the inner tube. The first probe is operatively associated with the bottom plate, and the second probe is operatively associated with the upper end of the material sample. Other means for measuring the deformation of the material sample include a laser interferometer, a strain gauge extensometer and a capacitance gauge.

When compressive force is applied, the force is transmitted from the inner tube to the material sample by a push member interposed between the lowermost annular plug within the inner tube and the material sample.

The inner tube and said outer tube are most preferably formed of a glass reinforced plastic composition. The annular plugs and annular sleeves are most preferably formed of stainless steel.

The apparatus most preferably further comprises means for measuring the amount of force applied to the material sample, such as a load cell.

BRIEF DESCRIPTION OF THE DRAWINGS

FIG. 3 is a sectional view of the lower portion of the displacement measuring assembly, which includes a linear variable differential transformer (LVDT), and further illustrating the mounting of the material sample on the bottom plate.

FIG. 4 is a top view taken in the direction of arrows 4—4 of FIG. 3, showing the lowermost annular plug associated with the inner tube and the push blade for applying force to the material sample, and further illustrating the tube, rod and probes of the displacement measuring assembly.

FIG. 5 is a side sectional view of a second embodiment of the present apparatus employing a displacement measuring assembly with three probes.

DETAILED DESCRIPTION OF THE DRAWINGS

Figure 1:
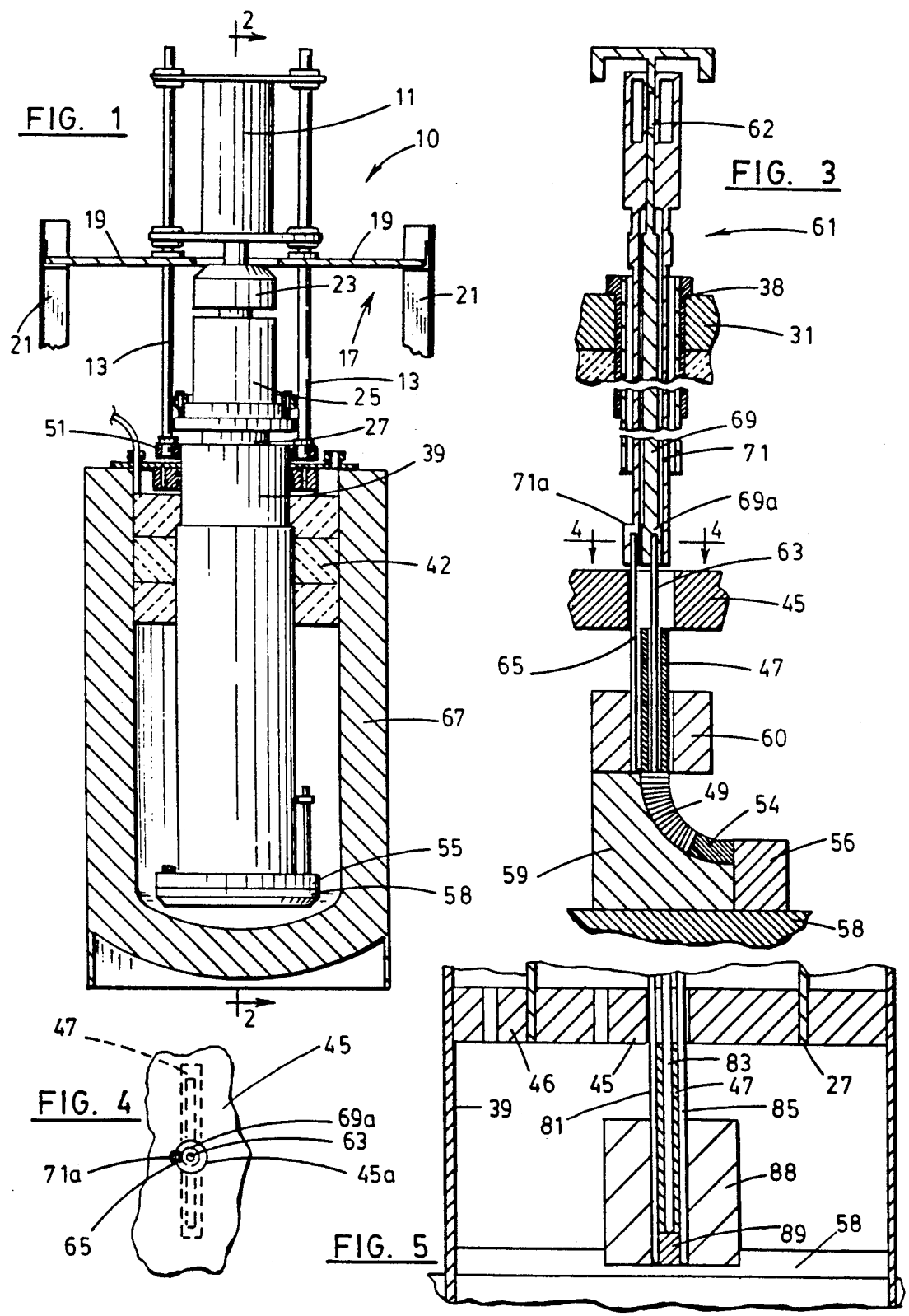
FIG. 1 is a side view, partly in section, of one embodiment of the present apparatus showing the stationary frame, the hydraulic cylinder for applying force to the material sample, and the outer tube, inner tube, insulation and base plate within the dewar.

Turning first to FIG. 1 of the drawings, a side view of the apparatus 10 for measuring tensile and compressive properties of solid materials is shown. Apparatus 10 includes stationary frame 17, which in turn includes angle iron frames 21 and support plate 19. FIG. 1 shows the exterior of double-action hydraulic cylinder 11 for applying force to the material sample (not shown) within dewar 67, load cell 23, dome member 25, and the upper portion of inner tube 27. Inner tube 27 is coaxial with and extends downwardly within outer tube 39. Both inner tube 27 and outer tube 39 extend downwardly within dewar 67, as shown in FIG. 1. Dewar 67 contains a liquid refrigerant, such as liquid nitrogen or liquid helium, to impart the cryogenic environment within dewar 67.

As further shown in FIG. 1, outer tube 39 is suspended from support plate 19 by threaded rods 13, which extend through the sleeve 51 shrink-fitted to the upper end of outer tube 39. Bottom plate 58 is bolted to the sleeve 55 shrink-fitted to the lower end of outer tube 39. In operation, force generated by cylinder 11 is transmitted through load cell 23 and dome member 25 to inner tube 27, which applies the actual force to the material sample mounted on a sample holder (not shown) extending upwardly from bottom plate 58.

Figure 2:
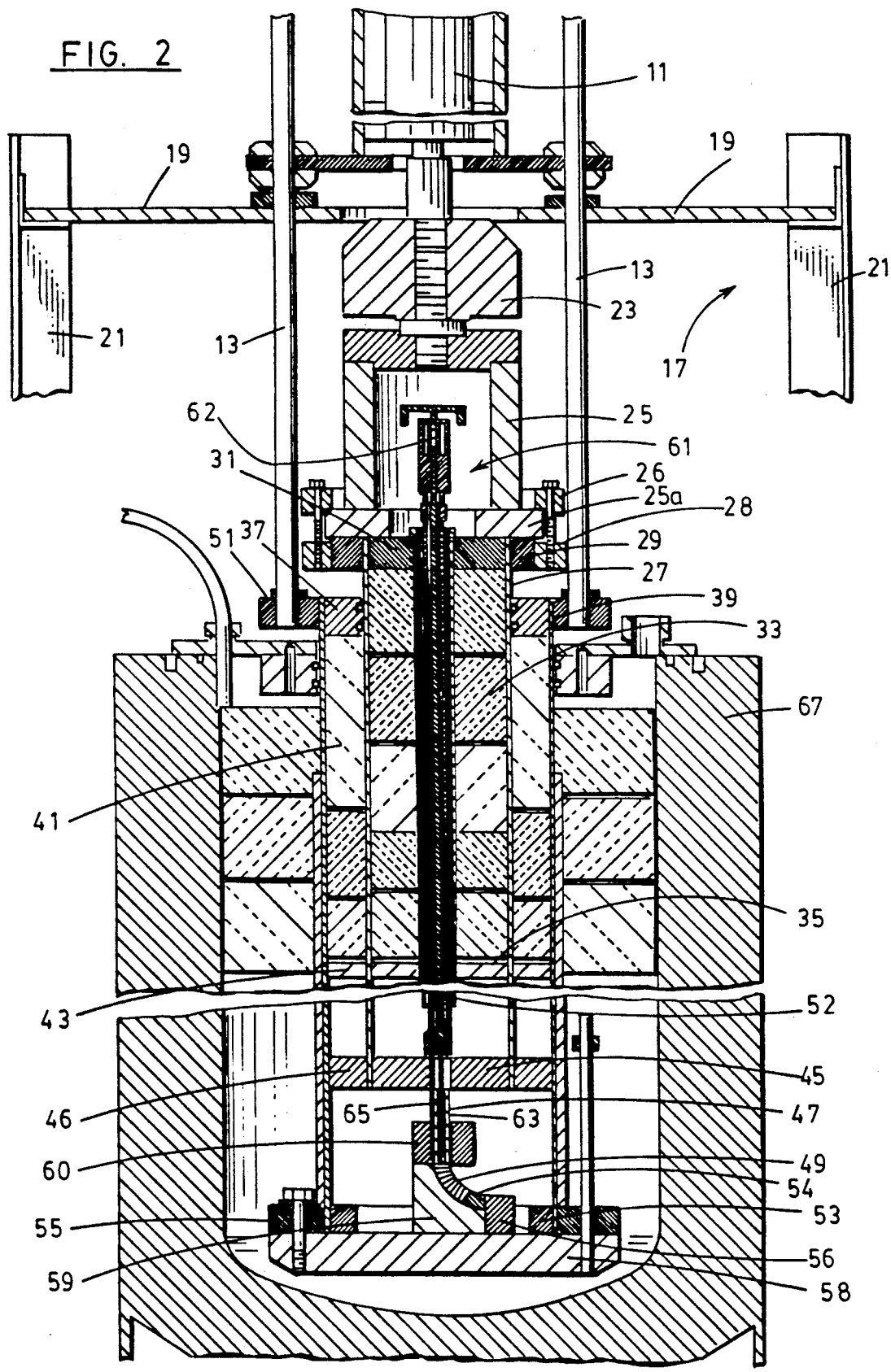
FIG. 2 is a sectional view of the apparatus taken in the direction of arrows 2—2 of FIG. 1.

Turning next to FIG. 2, double-action hydraulic cylinder 11 provides the compressive and tensile forces to be applied to the material sample. Hydraulic cylinder 11 is suspended above support plate 19 by threaded rods 13. Support plate 19 rests on angle iron frames 21. Frames 21 are stationary. The force generated by the double-action hydraulic cylinder 11 is measured by load cell 23. The force is conducted through load cell 23 and dome member 25 to the upper end of inner tube 27. Inner tube 27 is attached to dome member 25 and its extension 25a by bolts extending through dome member fittings 26 and sleeve fittings 28. Fittings 28 are affixed to upper annular sleeve 29. A shrink-fitted connection is formed between inner tube 27 and upper annular sleeve 29.

Fittings 26 and 28 are designed primarily for the application of compressive force from dome member 25 to inner tube 27. In applying tensile force to the material sample, sleeve 29 should be bolted directly to dome member extension 25a to adequately transmit the tensile force from dome member 25 to inner tube 27.

Upper annular plug 31 is shrink-fitted inside of inner tube 27 and provides a force to counterbalance the force exerted by upper sleeve 29. Middle annular sleeve 43 and middle annular plug 35 are shrink-fitted to the middle portion of inner tube 27 to prevent bulking of inner tube 27 when a compressive force is applied. Lower annular sleeve 46 and lower annular plug 45 are shrink-fitted to inner tube 27 at the bottom, as shown in FIG. 2. Insulation 33 is disposed between upper annular plug 31 and middle annular plug 35, as shown.

As further illustrated in FIG. 2, upper annular sleeve 51 and upper annular plug 37 are shrink-fitted to outer tube 39 at the top. Lower annular sleeve 55 and lower annular plug 53 are shrink-fitted to outer tube 59 the bottom. Insulation 41 is disposed between upper plug 37 of outer tube 39 and middle sleeve 43 of inner tube 27. Threaded rods 13 extend through upper sleeve 51 to suspend outer tube 39 from support plate 19.

Bottom plate 58 is fastened by bolts to sleeve 54, as shown in FIG. 2. Sample holder 59 extends upwardly from bottom plate 58. Material sample 49 is mounted in sample holder 59, as shown. FIG. 2 also shows sample stop block 56 and spacer element 54. In operation, inner tube 27 transmits force through plug 45 to urge push blade 47 against material sample 49.

As further shown in FIG. 2, the displacement measuring assembly 61, which employs a linear variable differential transformer ("LVDT") 62, includes two probes 63 and 65. Probe 63 rests on the upper end of material sample 49. Probe 65 rests on sample holder 59.

FIG. 3 illustrates the displacement measuring assembly 61, which includes LVDT 62. As shown, rod 69 extends downwardly from the center of LVDT 62, within tube 71. LVDT 62 detects the relative movement of rod 62 within tube 71. Guide tube 38 is attached to annular plug 31 at the top of the inner tube (not shown in FIG. 3). The interior of guide tube 38 forms the channel through which rod 62 and tube 71 extend. Rod 69 terminates at its lowermost end in a socket 69a. Similarly, tube 71 terminates at its lowermost end in a socket 71a. Probe 63 projects from socket 69a, and rests at its lowermost end on material sample 49. Probe 65 projects from socket 71a, and rests at its lowermost end on sample holder 59. Probes 63 and 65, rod 69, tube 71, and sockets 69a and 71a are preferable formed of quartz, although other materials having low coefficients of thermal expansion could also be employed. Sockets 69a and 71a permit probes 63 and 65 to be disconnected from rod 69 and tube 71 during the manual mounting of the material sample, and then reassembled for actual measurement of the tensile or compressive properties of the material sample.

FIG. 3 further illustrates the mounting of material sample 49 on bottom plate 58. As shown in FIG. 3, the sample holding assembly includes sample holder 59 extending upwardly from bottom plate 58, stop block 56, spacer element 54, and guide block 60. Although illustrated as separate components in FIG. 3, sample holder 59 and stop block 56 could be formed from a single block of material.

Turning now to FIG. 4, lowermost annular plug 45 is formed with a circular opening 45a to permit the passage of probes 63 and 65. Probes 63 and 65 extend downwardly from sockets 69a and 71a, respectively. When urged downwardly, annular plug 45 urges push blade 47 (shown in phantom lines in FIG. 4) against the upper end of the material sample.

FIG. 5 shows a cross-sectional view of second type of displacement measuring assembly having three probes 81, 83 and 85. Probes 81 and 85 rest on bottom plate 58, while probe 83 rests on the upper end of sample 89. Push member 47 exerts force against sample 89, which is mounted in guide block 88. Also shown in FIG. 5 are the lowermost ends of inner tube 27, annular plug 45, annular sleeve 46, and the lowermost end of outer tube 39.

Figure 6:
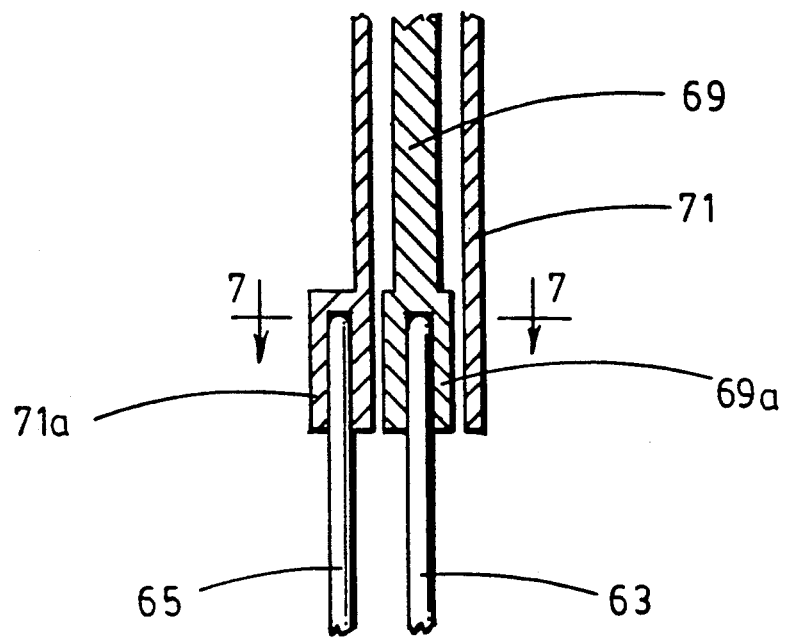
FIG. 6 is a cross-sectional view of the two probes associated with the displacement measuring assembly of FIG. 3.
Figure 7:
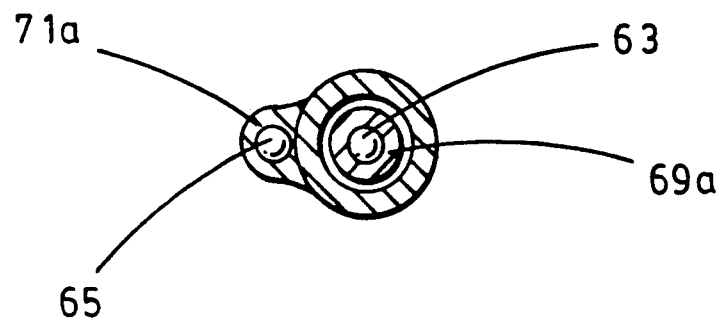
FIG. 7 is a cross sectional view taken in the direction of arrows 7—7 of FIG. 6.

Turning now to FIGS. 6 and 7, the lower portion of displacement measuring assembly 61 is shown. Two probes 63 and 65 extend from sockets 69a and 71a attached to tube 71 and rod 69, respectively. Tube 71 and rod 69 extend downwardly from LVDT 62 (not shown). Probe 63 rests on the upper end of the material sample (not shown) while probe 65 rests on the sample holder (not shown). As the material sample 49 is deformed by the application of force, probe 63 is displaced with respect to probe 65. The LVDT measures the difference in the relative positions of the ends of the two probes, thereby determining the strain or displacement of the material sample relative to the sample holder.

Referring again to FIG. 2, in operation, bottom plate 58 is lowered from sleeve 55 to initiate the sample mounting operation. A deformable material sample 49 is placed in sample holder 59 and stop block is positioned as shown, employing spacer element 54 as appropriate. After guide block 60 is positioned above sample holder 59 containing material sample 49, probes 63 and 65 and push blade 47 are mounted in guide block 60. Bottom plate 58 is then lifted into position against sleeve 55 by guiding probes 63 and 65 through the circular opening in annular plug 45 and into sockets 69a and 71a to complete the sample mounting operation. In conducting the tensile or compression testing, a tensile or compressive force is applied to the material sample by actuating the double action hydraulic cylinder 11 and determining from load cell 23 the amount of the force imposed. The force is then transmitted by dome member 25 to inner tube 27, which moves vertically within outer tube 39 to impart the force to material sample 49. The deformation of the material sample 49 is measured by the displacement measuring assembly 61, which determines the difference in the relative movement of probes 63 and 65. Probe 65 moves downwardly with material sample 49 as a compressive force is applied. Alternatively, probe 65 moves upwardly with material sample 49 as a tensile force is applied. The compressive and tensile properties of material sample 49 can be determined continuously as the amount of force is varied. Graphical depictions of the tensile and compressive properties of the material (i.e., stress-strain curves) can be generated from the force and deformation measurements.

The present invention can be retrofitted onto and used in conjunction with a conventional tensile property measuring apparatus, such as those produced by Instron Corporation.

While particular applications of the present invention have been shown, it will be understood, of course, that the invention is not limited thereto since modifications may be made by those skilled in the art, particularly in light of the foregoing teachings. It is therefore, contemplated that the appended claims cover any such modifications and incorporate those features which come within the true spirit and scope of the claims.

What is claimed is:

1. An apparatus for measuring the deformation of a material sample maintained at cryogenic temperatures in response to the application of compressive and tensile force, said apparatus comprising:
   a stationary frame maintained at ambient temperature;
   a dewar mounted below said frame, said dewar maintaining a cryogenic environment therein;
   an outer cylindrical tube extending downwardly within said dewar, said outer tube having an upper and a lower end, the upper end of said outer tube fixedly attached to said frame;
   a bottom plate fixedly attached to the lower end of said outer tube, said bottom plate adapted to support the material sample;
   an inner cylindrical tube extending downwardly within said outer tube, said inner tube having a upper end and a lower end, the lower end of said inner tube adapted to transmit a force to the material sample;
   means for applying a predetermined force to the upper end of said inner cylindrical tube;
   means for measuring the deformation of the material sample by measuring the displacement relative to said bottom plate, whereby the force applied to the upper end of said inner tube displaces said inner tube within said outer tube, thereby causing a measurable displacement of a portion of the material sample relative to the bottom plate.

2. The apparatus of claim 1 wherein each of the ends of said inner and outer tubes has an annular plug fitted within its interior surface and annular sleeve fitted over its exterior surface.

3. The apparatus of claim 2 wherein the annular sleeve of said outer tube is attached to said frame.

4. The apparatus of claim 2 wherein said annular plugs and said annular sleeves are attached to said inner and outer tubes by shrink-fitting.

5. The apparatus of claim 1 further comprising means for insulating the voids formed between said dewar and said outer tube, between said outer tube and said inner tube, and within said inner tube.

6. The apparatus of claim 1 wherein said means for measuring the deformation of the material sample is a linear variable differential transformer having a first probe and a second probe, said probes extending downwardly within said inner tube, said first probe operatively associated with said bottom plate, said second probe operatively associated with the material sample.

7. The apparatus of claim 2 wherein said predetermined force is a compressive force and said compressive force is transmitted from said inner tube to said material sample by a push member interposed between the lowermost annular plug within said inner tube and said material sample.

8. The apparatus of claim 1 wherein said inner tube and said outer tube are formed of a glass reinforced plastic composition.

9. The apparatus of claim 2 wherein said annular plugs and said annular sleeves are formed of stainless steel.

10. The apparatus of claim 1 further comprising means for measuring the amount of force applied to the material sample.

11. The apparatus of claim 1 wherein said dewar contains a liquid refrigerant.

12. The apparatus of claim 11 wherein said refrigerant is liquid helium.

* * * * *